US011058673B2

(12) United States Patent
Tse et al.

(10) Patent No.: US 11,058,673 B2
(45) Date of Patent: Jul. 13, 2021

(54) DOSAGE REGIMEN OF MDM2 INHIBITOR FOR TREATING CANCERS

(71) Applicant: DAIICHI SANKYO COMPANY, LIMITED, Tokyo (JP)

(72) Inventors: Ngai-chiu Archie Tse, Long Island, NY (US); Shengli Cai, Lake Hopatcong, NJ (US)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 16/293,926

(22) Filed: Mar. 6, 2019

(65) Prior Publication Data

US 2019/0201386 A1 Jul. 4, 2019

Related U.S. Application Data

(63) Continuation of application No. 15/769,054, filed as application No. PCT/JP2016/081975 on Oct. 21, 2016, now abandoned.

(60) Provisional application No. 62/245,632, filed on Oct. 23, 2015.

(51) Int. Cl.
*A61K 31/4439* (2006.01)
*A61P 35/00* (2006.01)
*A61K 9/00* (2006.01)

(52) U.S. Cl.
CPC ........ *A61K 31/4439* (2013.01); *A61K 9/0053* (2013.01); *A61P 35/00* (2018.01)

(58) Field of Classification Search
CPC .... A61K 31/4439; A61K 9/0053; A61P 35/00
See application file for complete search history.

(56) References Cited

U.S. PATENT DOCUMENTS

| | | | |
|---|---|---|---|
| 8,629,133 B2 | 1/2014 | Sugimoto et al. | |
| 9,359,368 B2 | 6/2016 | Yoshida et al. | |
| 9,540,386 B2 | 1/2017 | Yoshida et al. | |
| 9,718,830 B2 | 8/2017 | Yoshida et al. | |
| 9,718,831 B2 | 8/2017 | Yoshida et al. | |
| 9,745,315 B2 | 8/2017 | Yoshida et al. | |
| 9,884,871 B2 | 2/2018 | Yoshida et al. | |
| 10,023,578 B2 | 7/2018 | Yoshida et al. | |
| 10,030,030 B2 | 7/2018 | Yoshida et al. | |
| 2012/0264738 A1 | 10/2012 | Sugimoto et al. | |
| 2015/0210707 A1 | 7/2015 | Yoshida et al. | |
| 2017/0216302 A1 | 8/2017 | Seki | |

FOREIGN PATENT DOCUMENTS

| | | | |
|---|---|---|---|
| CN | 103635473 A | 3/2014 | |
| CN | 104812757 A | 7/2015 | |
| EP | 2894156 A1 | 7/2015 | |
| EP | 3284466 A1 | 2/2018 | |
| WO | WO-2012/121361 A1 | 9/2012 | |
| WO | WO-2015/108175 A1 | 7/2015 | |
| WO | WO-2016/133194 A1 | 8/2016 | |
| WO | WO-2016/167236 A1 | 10/2016 | |

OTHER PUBLICATIONS

Isabelle Ray-Coquard et al., Effect of the MDM2 antagonist RG7112 on the P53 pathway in patients with MDM2-amplified, well-differentiated or dedifferentiated liposarcoma: an exploratory proof-of-mechanism study, Lancet Oncol 2012; 13: 1133-40 (Year : 2012).*
Keith T. Flaherty et al. Phase I, Dose-Escalation Trial of the Oral Cyclin-Dependent Kinase 4/6 Inhibitor PD 0332991, Administered Using a 21-Day Schedule in Patients with Advanced Cancer, Clin Cancer Res; 18(2) Jan. 15, 2012 (Year: 2012).*
ALRN-6924 in Patients With Advanced Solid Tumors or Lymphomas, First Posted Oct. 15, 2014 (Year: 2014).*
Steinman H A et al. (2004), "An Alternative Splice Form of Mdm2 Induces p53-independent Cell Growth and Tumorigenesis", J Biol Chem, vol. 279, No. 6, pp. 4877-4886.
Coindre J-M et al. (2010), "Well-differentiated and dedifferentiated liposarcomas", Virchows Arch, 456: 167-179.
Momand J et al. (1998), "Survey and Summary: The MDM2 gene amplification database", Nucleic Acids Research, vol. 26, No. 15, pp. 3453-3459.
Rayburn E et al. (2005), "MDM2 and Human Malignancies: Expression, Clinical Pathology, Prognostic Markers, and Implications for Chemotherapy", Current Cancer Drug Targets, 5: 27-41.
Ray-Coquard I et al. (2012), "Effect of the MDM2 antagonist RG7112 on the P53 pathway in patients with MDM2-amplified, well-differentiated or dedifferentiated liposarcoma: an exploratory proof-of-mechanism study", Lancet Oncol, 13: 1133-1140.
International Search Report for International Application No. PCT/JP2016/081975 dated Feb. 1, 2017.
Office Action dated Mar. 16, 2020 for correpsonding Chinese Patent Application No. 201680061650.4.
Zhang Ruming—Feb. 28, 2010—Tianjin Science and Technology Press; p. 72.
Anonymous. (2016) "Sarcoma". Oncology Forum. Diagnosis and Treatment and Case Discussion. Tumor Forum [online]. Retrieved from: http://www.cancertreatmentcn.com/solid-tumor/%E8%82%89%E7%98%A4/, retrieved on Jul. 6, 2020; 3 pages with 3 pages of translation.
Siu, L.L. et al. (2014) "Phase 1 dose escalation, food effect, and biomarker study of RG7388, a more potent second-generation MDM2 antagonist, in patients (pts) with solid tumors" J Clin Oncol, 32(15 Suppl):Abstract 2535; DOI: 10.1200/jco.2014.32.15_suppl.2535, 2 printed pages.

* cited by examiner

*Primary Examiner* — Sarah Pihonak
*Assistant Examiner* — Jason Deck
(74) *Attorney, Agent, or Firm* — Cooley LLP; J. Dean Farmer; Christine E. Dunne

(57) ABSTRACT

The present invention provides a method for treating a cancer in a subject in need thereof, comprising administering a specific MDM2 inhibitor to the subject according to a specific dosage regimen and a pharmaceutical composition for use in treating a cancer according to the dosage regimen. The present invention also provides a method for treating liposarcoma in a subject in need thereof, comprising administering a specific MDM2 inhibitor to the subject and a pharmaceutical composition for use in treating liposarcoma, comprising the MDM2 inhibitor.

38 Claims, 2 Drawing Sheets

DOSAGE REGIMEN OF MDM2 INHIBITOR FOR TREATING CANCERS

CROSS-REFERENCE TO RELATED APPLICATIONS

This application is a Continuation of U.S. patent application Ser. No. 15/769,054, filed on Apr. 17, 2018, which is a National Stage Entry of International Patent Application No. PCT/JP2016/081975, filed on Oct. 21, 2016, which claims the benefit of priority of U.S. Provisional Patent Application No. 62/245,632, filed on Oct. 23, 2015. The entire contents of which are hereby incorporated by reference in their entireties.

FIELD OF THE INVENTION

The present invention relates to a method for treating a cancer in a subject in need thereof, comprising administering a specific MDM2 inhibitor to the subject according to a specific dosage regimen and a pharmaceutical composition for use in treating a cancer according to the dosage regimen. The present invention also relates to a method for treating liposarcoma in a subject in need thereof, comprising administering a specific MDM2 inhibitor to the subject and a pharmaceutical composition for use in treating liposarcoma, comprising the MDM2 inhibitor.

BACKGROUND OF THE INVENTION

MDM2, located on Chromosome 12 q13-15, is a negative regulator of the p53 tumor suppressor protein. The 90 kDa MDM2 protein contains a p53 binding domain at its N-terminus and a RING (really interesting new gene) domain at its C-terminus, which functions as an E3 ligase that ubiquitinates p53. The activation of wild-type p53 by cell stimuli and stresses results in the binding of MDM2 to p53 at the N-terminus to inhibit the transcriptional activation of p53 and promote the degradation of p53 via the ubiquitin-proteasome pathway. Thus, MDM2 can interfere with p53-mediated apoptosis and arrest of cancer cell proliferation, attributing a significant oncogenic activity to MDM2 in cancer cells. In some cases, MDM2 can cause carcinogenesis independent of the p53 pathway, for example, in cells which possess an alternative splice form of MDM2 (H. A. Steinman et al., 2004, J. Biol. Chem., 279(6):4877-4886). Therefore, several MDM2 inhibitors have been developed to treat cancers, including (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydro-dispiro[cyclohexane-1,2'-pyrrolidine-3',3''-indole]-5'-carboxamide (WO2012/121361 and US Patent Application Publication No. 2012/0264738A).

Liposarcoma (LPS) is one of the most common soft tissue sarcoma (STS) subtype, comprising about 18 to 26% of STS cases in humans. LPS can be categorized into four subtypes: well-differentiated type (WD, 46 to 54%), de-differentiated type (DD, 18 to 26%), myxoid/round-cell type (13 to 28%) and pleomorphic type (7 to 8%). Chromosome 12 q13-15 amplification is frequently found in WD/DD LPS (i.e. up to ~90% of patients) (Coindre et al., 2010, Virchows. Arch., 456:167-179, Momand et al., 1998, Nucleic Acid Research, 26 (15):3453-3459, and Rayburn et al., 2005, Current Cancer Drug Targets, 5:27-41). Thus, some of the MDM2 antagonists were developed as a therapeutic drug for liposarcoma (Ray-Coquard et al., 2012, Lancet Oncol., 13:1133-1140).

SUMMARY OF THE INVENTION

The present invention provides a method for treating a cancer in a subject in need thereof, comprising administering a specific MDM2 inhibitor to the subject according to a specific dosage regimen and a pharmaceutical composition for use in treating a cancer according to the dosage regimen. The present invention also provides a method for treating liposarcoma in a subject in need thereof, comprising administering a specific MDM2 inhibitor to the subject and a pharmaceutical composition for use in treating liposarcoma, comprising the MDM2 inhibitor.

The inventors have discovered that solid cancers and lymphoma can be treated by orally administering to the subjects (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide (hereinafter also referred to as "Compound") or pharmaceutically acceptable salt thereof according to a dosage schedule, wherein the dosage schedule comprises administering a daily dose of 80 to 250 mg of the compound or salt thereof to the subject in a cyclical dosing (QD21/28 or QD28/28). The inventors have also discovered that liposarcoma can be treated with Compound 1.

The present invention provides:
(1) A pharmaceutical composition for use in treating a cancer in a subject in need thereof, comprising a therapeutically effective amount of the compound of formula (I) or pharmaceutically acceptable salt thereof, wherein the pharmaceutical composition is orally administered according to a dosage schedule comprising administering a daily dose of about 80 mg to about 250 mg of the compound or salt thereof to the subject.

[Chem. 1]

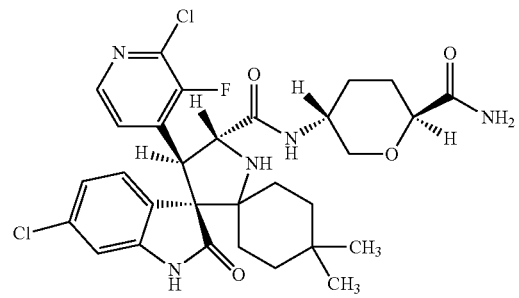

(I)

(3'R,4'S,5'R)—N-[(3R,6S)-6-Carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide (2) A pharmaceutical composition according to above (1), wherein the dosage schedule comprises administering a daily dose of about 80 mg to about 140 mg of the compound or salt thereof to the subject.

(3) A pharmaceutical composition according to above (1), wherein the dosage schedule comprises administering a daily dose of about 80 mg to about 100 mg of the compound or salt thereof to the subject.

(4) A pharmaceutical composition according to above (1), wherein the dosage schedule comprises administering a daily dose of about 90 mg of the compound or salt thereof to the subject.

(5) A pharmaceutical composition according to above (1), wherein the dosage schedule comprises administering a daily dose of about 100 mg to about 140 mg of the compound or salt thereof to the subject.

(6) A pharmaceutical composition according to above (1), wherein the dosage schedule comprises administering a daily dose of about 120 mg of the compound or salt thereof to the subject.

(7) A pharmaceutical composition for use in treating a cancer in a subject in need thereof according to any one of above (1) to (6), wherein the cancer is liposarcoma.

(8) A pharmaceutical composition for use in treating a cancer in a subject in need thereof according to above (7), wherein the cancer is a liposarcoma having amplified MDM2 genes in the genome of the liposarcoma.

(9) A pharmaceutical composition for use in treating a cancer in a subject in need thereof, comprising a therapeutically effective amount of the compound of formula (I) or pharmaceutically acceptable salt thereof, wherein the pharmaceutical composition is orally administered for at least one cycle of a cyclical dosing schedule, wherein each cycle has a dosing period of at least 10 days, in which the compound or salt thereof is administered daily at a daily dosage of about 80 mg to about 250 mg.

(10) A pharmaceutical composition according to above (9), wherein the compound or salt thereof is administered daily at a daily dosage of about 80 mg to about 140 mg.

(11) A pharmaceutical composition according to above (9), wherein the compound or salt thereof is administered daily at a daily dosage of about 80 mg to about 100 mg.

(12) A pharmaceutical composition according to above (9), wherein the compound or salt thereof is administered daily at a daily dosage of about 90 mg.

(13) A pharmaceutical composition according to above (9), wherein the compound or salt thereof is administered daily at a daily dosage of about 100 mg to about 140 mg.

(14) A pharmaceutical composition according to above (9), wherein the compound or salt thereof is administered daily at a daily dosage of about 120 mg.

(15) A pharmaceutical composition according to above (9), wherein the compound or salt thereof is administered daily at a daily dosage of about 140 mg to about 180 mg.

(16) A pharmaceutical composition according to above (9), wherein the compound or salt thereof is administered daily at a daily dosage of about 160 mg.

(17) A pharmaceutical composition according to above (9), wherein the compound or salt thereof is administered daily at a daily dosage of about 180 mg to about 250 mg.

(18) A pharmaceutical composition according to above (9), wherein the compound or salt thereof is administered daily at a daily dosage of about 210 mg.

(19) A pharmaceutical composition for use in treating a cancer in a subject in need thereof, comprising a therapeutically effective amount of the compound of formula (I) or pharmaceutically acceptable salt thereof, wherein the pharmaceutical composition is orally administered for at least one cycle of a cyclical dosing schedule, wherein each cycle has a dosing period of about 15 days to about 25 days, in which the compound or salt thereof is administered daily at a daily dosage of about 80 mg to about 250 mg of the compound or salt thereof, followed by a rest period of about 5 days to about 10 days in which any of the compound and salt thereof is not administered.

[Chem. 1]

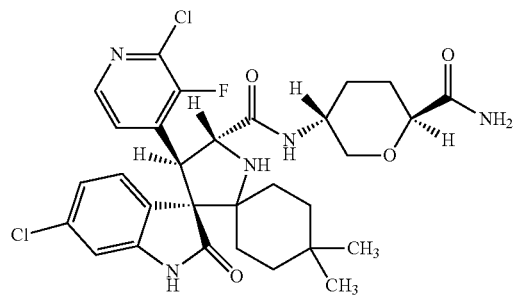

(I)

(3'R,4'S,5'R)—N-[(3R,6S)-6-Carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide

(20) A pharmaceutical composition according to any one of above (9) to (19), wherein each cycle has a dosing period of about 15 days to about 25 days, in which the compound or salt thereof is administered daily at a daily dosage of about 100 mg to about 140 mg, followed by a rest period of about 5 days to about 10 days, in which any of the compound and salt thereof is not administered.

(21) A pharmaceutical composition according to any one of above (9) to (19), wherein each cycle has a dosing period of about 15 days to about 25 days, in which the compound or salt thereof is administered daily at a daily dosage of about 120 mg, followed by a rest period of about 5 days to about 10 days, in which any of the compound and salt thereof is not administered.

(22) A pharmaceutical composition according to any one of above (9) to (19), wherein each cycle has a dosing period of about 15 days to about 25 days, in which the compound or salt thereof is administered daily at a daily dosage of about 140 mg to about 180 mg, followed by a rest period of about 5 days to about 10 days, in which any of the compound and salt thereof is not administered.

(23) A pharmaceutical composition according to any one of above (9) to (19), wherein each cycle has a dosing period of about 15 days to about 25 days, in which the compound or salt thereof is administered daily at a daily dosage of about 160 mg, followed by a rest period of about 5 days to about 10 days, in which any of the compound and salt thereof is not administered.

(24) A pharmaceutical composition according to any one of above (9) to (19), wherein each cycle has a dosing period of about 15 days to about 25 days, in which the compound or salt thereof is administered daily at a daily dosage of about 180 mg to about 250 mg, followed by a rest period of about 5 days to about 10 days, in which any of the compound and salt thereof is not administered.

(25) A pharmaceutical composition according to any one of above (9) to (19), wherein each cycle has a dosing period of about 15 days to about 25 days, in which the compound or salt thereof is administered daily at a daily dosage of about 210 mg, followed by a rest period of about 5 days to about 10 days, in which any of the compound and salt thereof is not administered.

(26) A pharmaceutical composition according to any one of above (9) to (19), wherein each cycle has a dosing period of about 21 days, in which the compound or salt thereof is administered daily at a daily dosage of about 100 mg to about 140 mg, followed by a rest period of about 7 days, in which any of the compound and salt thereof is not administered.

(27) A pharmaceutical composition according to any one of above (9) to (19), wherein each cycle has a dosing period of about 21 days, in which the compound or salt thereof is administered daily at a daily dosage of about 140 mg to about 180 mg, followed by a rest period of about 7 days, in which any of the compound and salt thereof is not administered.

(28) A pharmaceutical composition according to any one of above (9) to (19), wherein each cycle has a dosing period of about 21 days, in which the compound or salt thereof is administered daily at a daily dosage of about 180 mg to about 250 mg, followed by a rest period of about 7 days, in which any of the compound and salt thereof is not administered.

(29) A pharmaceutical composition according to any one of above (9) to (19), wherein each cycle has a dosing period of about 15 days to about 25 days, in which the compound or salt thereof is administered daily at a daily dosage of about 80 mg to about 100 mg, followed by a rest period of about 5 days to about 10 days, in which any of the compound and salt thereof is not administered.

(30) A pharmaceutical composition according to any one of above (9) to (19), wherein each cycle has a dosing period of about 15 days to about 25 days, in which the compound or salt thereof is administered daily at a daily dosage of about 90 mg, followed by a rest period of about 5 days to about 10 days, in which any of the compound and salt thereof is not administered.

(31) A pharmaceutical composition according to any one of above (9) to (19), wherein each cycle has a dosing period of about 21 days, in which the compound or salt thereof is administered daily at a daily dosage of about 80 mg to about 100 mg, followed by a rest period of about 7 days, in which any of the compound and salt thereof is not administered.

(32) A pharmaceutical composition according to any one of above (9) to (19), wherein each cycle has a dosing period of about 21 days, in which the compound or salt thereof is administered daily at a daily dosage of about 120 mg of the compound or salt thereof, followed by a rest period of about 7 days, in which any of the compound and salt thereof is not administered.

(33) A pharmaceutical composition according to any one of above (9) to (19), wherein each cycle has a dosing period of about 21 days, in which the compound or salt thereof is administered daily at a daily dosage of about 160 mg of the compound or salt thereof, followed by a rest period of about 7 days, in which any of the compound and salt thereof is not administered.

(34) A pharmaceutical composition according to any one of above (9) to (19), wherein each cycle has a dosing period of about 21 days, in which the compound or salt thereof is administered daily at a daily dosage of about 210 mg of the compound or salt thereof, followed by a rest period of about 7 days, in which any of the compound and salt thereof is not administered.

(35) A pharmaceutical composition according to any one of above (9) to (19), wherein each cycle has a dosing period of about 21 days, in which the compound or salt thereof is administered daily at a daily dosage of about 90 mg of the compound or salt thereof, followed by a rest period of about 7 days, in which any of the compound and salt thereof is not administered.

(36) A pharmaceutical composition for use in treating a cancer in a subject in need thereof according to any one of above (9) to (35), wherein the cancer is liposarcoma.

(37) A pharmaceutical composition for use in treating a cancer in a subject in need thereof according to above (36), wherein the cancer is a liposarcoma having amplified MDM2 genes in the genome of the liposarcoma.

(38) A pharmaceutical composition for use in treating a cancer in a subject in need thereof according to any one of above (1) to (37), wherein the compound or salt thereof is in a form of p-toluenesulfonic acid salt monohydrate (hereinafter also referred to as "Compound 2") as shown in formula (II).

[Chem. 2]

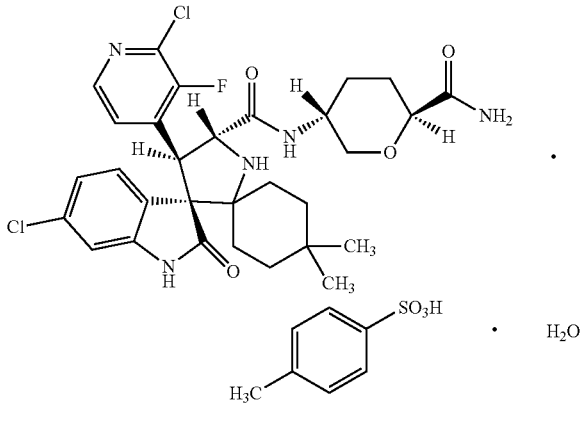

(II)

(39) A pharmaceutical composition for use in treating liposarcoma, comprising (3'R,4'S,5'R)—N-[(3R,6S)-6-Carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or pharmaceutically acceptable salt thereof.

(40) A pharmaceutical composition according to above (39), wherein liposarcoma has amplified MDM2 genes in the genome of the liposarcoma.

BRIEF DESCRIPTION OF DRAWINGS

FIG. 2 is a waterfall plot showing the best tumor response in all the subjects suffering from liposarcoma in the clinical study (n=13). Subjects with WD and DD liposarcoma are indicated by the letter 'WD' and "DD" above the bars, respectively. Baseline is defined as the last non-missing value taken before the first dose of Compound 2. For each subject, the best (minimum) percent change from baseline in the sum of diameters for all target lesions is represented by a vertical bar. The term "PD" and "SD" mean Progressive Disease and Stable Disease, respectively, as are defined in RECIST guidelines v1.1.

DETAILED DESCRIPTION OF THE INVENTION

Figure 1:
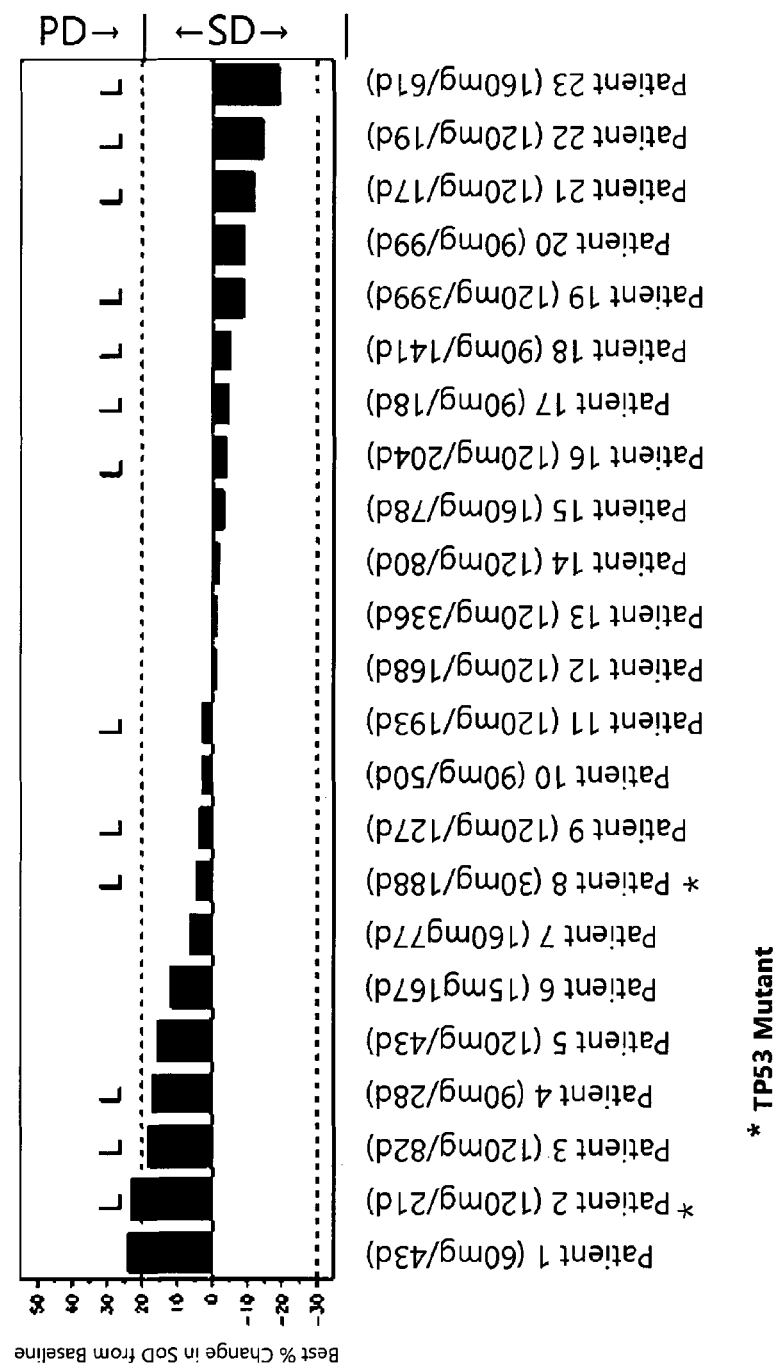
FIG. 1 is a waterfall plot showing the best tumor response in all the evaluable subjects in the clinical study (n=23). Subjects with liposarcoma are indicated by the letter "L" above the bars. Baseline is defined as the last non-missing value taken before the first dose of Compound 2. For each subject, the best (minimum) percent change from baseline in the sum of diameters for all target lesions is represented by a vertical bar. The term "PD" and "SD" mean Progressive Disease and Stable Disease, respectively, as are defined in RECIST guidelines v1.1.

The term "comprise" as used herein is intended to be an open-ended, inclusive and does not exclude additional, unrecited features, and then encompasses the closed term "consist of" or "essentially consist of".

The term "subject" refers to a mammal, especially a human, suffering or suspected of suffering from a cancer. The subject can be a subject which has been or was previously treated by other therapy. The subject can be an adult human.

The term "treat" refers to reducing the severity of the disease or slowing progression of the disease, which can be determined by physicians according to Response Evaluation in Solid Tumors guidelines (RECIST) version 1.1.

The term "MDM2" refers to an E3 ubiquitin ligase which can interact with p53 and cause p53 degradation. "MDM2" as used herein includes, but not limited to, mouse MDM2 and the human ortholog of MDM2 (also called "Human Double Minute 2" or "HDM2"). The term "MDM2 inhibitor" refers to an inhibitor inhibiting MDM2 functions or activities on p53 degradation.

The term "binding" refers generally to an interaction or association between two substances or molecules, such as the hybridization of one nucleic acid molecule to another (or to itself); the association of an antibody with a polypeptide, protein, or peptide; or the association of a protein with another protein or nucleic acid molecule. An oligonucleotide molecule binds or stably binds to a target nucleic acid molecule if a sufficient amount of the oligonucleotide molecule forms base pairs or is hybridized to its target nucleic acid molecule, to permit detection of that binding. Preferentially, binding refers to an association in which one molecule binds to another with high affinity, and binds to heterologous molecules at a low affinity. Binding can be detected by any procedure known to one skilled in the art, such as by physical or functional properties of the target/oligonucleotide complex. For example, binding can be detected functionally by determining whether there is an observable effect upon a biosynthetic process, e.g., expression of a gene, DNA replication, transcription, translation, etc.

The term "gene" as used herein refers to a DNA sequence which is expressed in a subject as an RNA transcript; a gene can be a full-length gene (protein encoding or non-encoding).

As used in accordance with the present invention, "gene expression" means the process of converting genetic information encoded in a gene into RNA (e.g., mRNA, rRNA, tRNA, or snRNA) through transcription of the gene (e.g., as mediated by the enzymatic action of an RNA polymerase), and for protein-encoding genes, into protein through "translation" of mRNA.

The term "cancer" as used herein is understood to encompass neoplasms and tumors, which refer to abnormal growths or abnormally growing cells that can invade surrounding tissues and spread to other organs, i.e., become malignant, if left untreated. Neoplasms are abnormal growths (or masses) of tissues comprised of cells that form as a result of neoplasia, which is the abnormal growth and proliferation of cells, either malignant or benign. Neoplasms and tumors can include the abnormal growths of precancerous and cancerous cells and tissues, which grow more rapidly than normal cells and that will continue to grow and compete with normal cells for nutrients if not treated. Neoplasms may include, without limitation, solid and non-solid tumors, such as hollow or liquid-filled tumors, and also hematological cell neoplasias or neoplasms, e.g., lymphomas, leukemias and myelomas.

The term "cancer" is also intended to embrace neoplasms and tumors of various origins within and on the body, various types and subtypes, as well as organ, tissue and cell samples and specimens, e.g., biological samples or specimens, thereof. Illustratively, appropriate cancer samples or specimens include any conventional biological samples or specimens, including clinical samples obtained from a human, e.g., a patient undergoing treatment for cancer, or a veterinary subject. A sample may refer to a part of a tissue that is a diseased or healthy portion of the tissue, or to the entire tissue. Tissue samples can be obtained from a subject by employing any method or procedure as known and practiced in the art.

The term "liposarcoma" is one of the most commons soft tissue sarcomas in adults that resemble fat cells in a histological section under a microscope. Liposarcoma represents about 18 to 26% of soft tissue sarcomas. According to its pathological study, liposarcomas can be classified into four subtypes: well-differentiated (WD, 46 to 54%), de-differentiated (DD, 18 to 26%), myxoid/round-cell (13 to 28%), and pleomorphic (7 to 8%) liposarcomas. Chromosome 12 q13-15 amplification is frequently found in a subject suffering from liposarcoma, such as WD or DD liposarcomas. It is known that MDM2 gene is located on Chromosome 12 q13-15 and therefore it is presumed that MDM2 genes are frequently amplified in a subject suffering from liposarcoma.

The term "pharmaceutically acceptable salt" refers to salts of the active compounds which are relatively nontoxic acid or base addition salts. Non-limited examples of the acid addition salts include hydrochloric, hydrobromic, nitric, carbonic, phosphoric, acetic, propionic, isobutyric, maleic, malonic, benzoic, succinic, fumaric, lactic, benzenesulfonic, p-toluenesulfonic, citric, tartaric, oxalic, and methanesulfonic acids. The term "pharmaceutically acceptable salt" includes pharmaceutically acceptable solvate or salt thereof. The solvate is a stoichiometric complex of a molecule and one or more solvent molecules. Non-limited examples of pharmaceutically acceptable solvates include water, methanol, ethanol, dimethylsulfoxide, and acetate as solvent. A solvate which contains water as solvent is hydrate. In a preferable embodiment of the invention, the pharmaceutically acceptable salt of the compound can be hydrate and more preferably monohydrate.

The term "about" used herein refers to the specific value subsequent to the term and a range of values±10% of the specific value. For example, the phrase "about 100" refers to 100, which is the specific value in this case, and a range of 90 to 110.

The compound of formula (I): (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide and pharmaceutically acceptable salts thereof, including the p-toluenesulfonate thereof, are disclosed as one of MDM2 inhibitors (see, Example 70 of WO 2012/121361 and Example 70 of US Patent Application Publication No. 2012/0264738A, which are incorporated by reference herein in its entirety).

[Chem. 1]

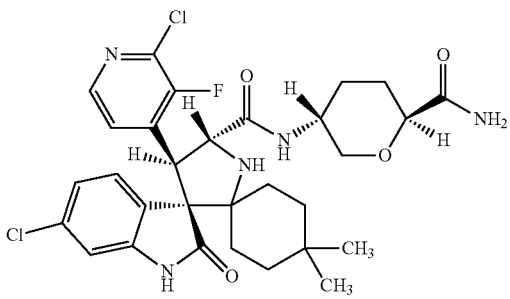

(I)

Unless otherwise indicated, the compound of formula (I) means the compound and pharmaceutically acceptable salt and pharmaceutically acceptable solvate, and prodrug thereof.

In one of the most preferable embodiments of the invention, this compound can be the compound of formula (II): (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide mono(4-methylbenzenesulfonate) monohydrate (also referred to as mono p-toluenesulfonate monohydrate of the compound).

[Chem. 2]

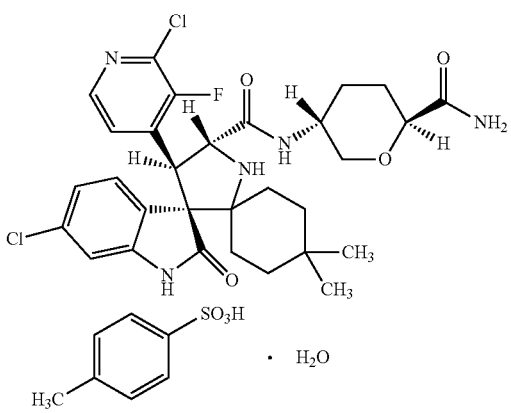

(II)

The compound of formula (I) can be administered once daily to a subject suffering from a cancer according to a dosage schedule of the present invention in order to treat the cancer in the subject.

In a preferable embodiment of the invention, the compound of formula (I) can be orally administered to the subject at a daily dose of about 80 mg to about 250 mg of the compound. In a particular embodiment of the invention, the compound of formula (I) can be orally administered to the subject at a daily dose of about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, or about 250 mg.

In a preferable embodiment of the invention, the compound of formula (I) can be orally administered to the subject at a daily dose of about 80 mg to about 140 mg, more preferably about 80 mg to about 100 mg, still more preferably about 90 mg of the compound for at least one week, two weeks, three weeks, four weeks or more.

In a preferable embodiment of the invention, the compound of formula (I) can be orally administered to the subject at a daily dose of about 100 mg to about 140 mg, more preferably about 120 mg of the compound for at least one week, two weeks, three weeks, four weeks or more. In another preferable embodiment of the invention, the compound of formula (I) can be orally administered to the subject at a daily dose of about 140 mg to about 180 mg, more preferably about 160 mg of the compound for at least one week, two weeks, three weeks, four weeks or more. In another preferable embodiment of the invention, the compound of formula (I) can be orally administered to the subject at a daily dose of about 180 mg to about 250 mg, more preferably about 210 mg of the compound for at least one week, two weeks, three weeks, four weeks or more.

In a preferable embodiment of the invention, the compound of formula (I) or pharmaceutically acceptable salt thereof is orally administered for at least one cycle of a cyclical dosing schedule, wherein each cycle has a dosing period of at least 10 days, in which the compound or salt thereof is administered daily at a daily dosage of about 80 mg to about 250 mg is provided. In this embodiment, the dosing period is preferably at least 15 days, more preferably between about 15 days to about 25 days, still more preferably about 21 days, and the daily dosage is preferably about 80 mg to about 100 mg or about 100 mg to 140 mg, more preferably about 90 mg or about 120 mg. In another embodiment, the dosing period is preferably at least 15 days, more preferably between about 15 days to about 25 days, still more preferably about 21 days, and the daily dosage is preferably about 140 mg to about 180 mg or about 180 mg to 250 mg, more preferably about 160 mg or about 210 mg. In a specific embodiment, the dosing period is at least 15 days and the daily dosage is about 80 mg to about 100 mg, more preferably about 90 mg. In another specific embodiment, the dosing period is at least 15 days and the daily dosage is about 100 mg to about 140 mg, more preferably about 120 mg. In a specific embodiment, the dosing period is at least 15 days and the daily dosage is about 140 mg to about 180 mg, more preferably about 160 mg. In another specific embodiment, the dosing period is at least 15 days and the daily dosage is about 180 mg to about 250 mg, more preferably about 210 mg.

In another preferable embodiment of the invention, the compound of formula (I) can be orally administered to the subject at a daily dose of about 100 mg to about 140 mg, more preferably about 120 mg of the compound for at least one cycle of a cyclical dosing schedule, wherein each cycle has a dosing period of about 15 days to about 25 days, in which the compound is administered daily at the above-mentioned dose, followed by a rest period of about 5 days to about 10 days in which any of the compounds is not administered. In a specific embodiment of the invention, the compound of formula (I) can be orally administered to the subject at a daily dose of about 120 mg of the compound for at least one cycle of a cyclical dosing schedule, wherein each cycle has a dosing period of about 15 days to about 25 days, more preferably about 21 days, in which the compound is administered daily at the above-mentioned dose, followed by a rest period of about 5 days to about 10 days, more preferably about 7 days in which any of the compounds is not administered. In a specific embodiment of the invention, the compound of formula (I) can be orally administered to the subject at a daily dose of about 120 mg of the compound for at least one cycle of a cyclical dosing schedule, wherein each cycle has a dosing period of about 21 days, in which the compound is administered daily at the above-mentioned dose, followed by a rest period of about 7 days in which any of the compounds is not administered.

In another preferable embodiment of the invention, the compound of formula (I) can be orally administered to the subject at a daily dose of about 80 mg to about 100 mg, more preferably about 90 mg of the compound for at least one cycle of a cyclical dosing schedule, wherein each cycle has a dosing period of about 15 days to about 25 days, in which the compound is administered daily at the above-mentioned dose, followed by a rest period of about 5 days to about 10 days in which any of the compounds is not administered. In more specific embodiment of the invention, the compound of formula (I) can be orally administered to the subject at a daily dose of about 90 mg of the compound for at least one cycle of a cyclical dosing schedule, wherein each cycle has a dosing period of about 15 days to about 25 days, more preferably about 21 days, in which the compound is administered daily at the above-mentioned dose, followed by a rest period of about 5 days to about 10 days, more preferably about 7 days in which any of the compounds is not administered. In a specific embodiment, the compound of formula (I) can be orally administered to the subject at a daily dose of about 90 mg of the compound for at least one cycle of a cyclical dosing schedule, wherein each cycle has a dosing period of about 21 days, in which the compound is administered daily at the above-mentioned dose, followed by a rest period of about 7 days in which any of the compounds is not administered.

In another preferable embodiment of the invention, the compound of formula (I) can be orally administered to the subject at a daily dose of about 140 mg to about 180 mg, more preferably about 160 mg of the compound for at least one cycle of a cyclical dosing schedule, wherein each cycle has a dosing period of about 15 days to about 25 days, in which the compound is administered daily at the above-mentioned dose, followed by a rest period of about 5 days to about 10 days in which any of the compounds is not administered. In a specific embodiment of the invention, the compound of formula (I) can be orally administered to the subject at a daily dose of about 160 mg of the compound for at least one cycle of a cyclical dosing schedule, wherein each cycle has a dosing period of about 15 days to about 25 days, more preferably about 21 days, in which the compound is administered daily at the above-mentioned dose, followed by a rest period of about 5 days to about 10 days, more preferably about 7 days in which any of the compounds is not administered. In a specific embodiment of the invention, the compound of formula (I) can be orally administered to the subject at a daily dose of about 160 mg of the compound for at least one cycle of a cyclical dosing schedule, wherein each cycle has a dosing period of about 21 days, in which the compound is administered daily at the above-mentioned dose, followed by a rest period of about 7 days in which any of the compounds is not administered.

In another preferable embodiment of the invention, the compound of formula (I) can be orally administered to the subject at a daily dose of about 180 mg to about 250 mg, more preferably about 210 mg of the compound for at least one cycle of a cyclical dosing schedule, wherein each cycle has a dosing period of about 15 days to about 25 days, in which the compound is administered daily at the above-mentioned dose, followed by a rest period of about 5 days to about 10 days in which any of the compounds is not administered. In a specific embodiment of the invention, the compound of formula (I) can be orally administered to the subject at a daily dose of about 210 mg of the compound for at least one cycle of a cyclical dosing schedule, wherein each cycle has a dosing period of about 15 days to about 25 days, more preferably about 21 days, in which the compound is administered daily at the above-mentioned dose, followed by a rest period of about 5 days to about 10 days, more preferably about 7 days in which any of the compounds is not administered. In a specific embodiment of the invention, the compound of formula (I) can be orally administered to the subject at a daily dose of about 210 mg of the compound for at least one cycle of a cyclical dosing schedule, wherein each cycle has a dosing period of about 21 days, in which the compound is administered daily at the above-mentioned dose, followed by a rest period of about 7 days in which any of the compounds is not administered.

In the invention, cancers to be treated includes, but not limited to, solid cancers and hematological cancers. Solid cancers to be treated in the invention include, but not limited to, soft tissue sarcoma, such as liposarcoma, melanoma, neuroendocrine cancer, adenoid cystic cancer, leiomyosarcoma, colorectal cancer, renal cancer, lung cancer, chordoma, salivary adenocarcinoma, adrenocortical carcinoma, and maxillary sinus adenocarcinoma. Hematological cancers to be treated in the invention include, but not limited to, lymphoma. In a preferable embodiment of the invention, solid cancers to be treated can be liposarcoma such as DD or WD liposarcoma.

The compound of formula (I) can act as an MDM2 inhibitor. MDM2 is a negative regulator of the p53 tumor suppressor protein. The 90 kDa MDM2 protein contains a p53 binding domain at its N-terminus and a RING (really interesting new gene) domain at its C-terminus, which functions as an E3 ligase that ubiquinates p53. The activation of wild-type p53 by cell stimuli and stresses results in the binding of MDM2 to p53 at the N-terminus to inhibit the transcriptional activation of p53 and promote the degradation of p53 via the ubiquitin-proteosome pathway. Thus, MDM2 can interfere with p53-mediated apoptosis and arrest of cancer cell proliferation, attributing a significant oncogenic activity to MDM2 in cancer cells. In some cases, MDM2 can cause carcinogenesis independent of the p53 pathway, for example, in cells which possess an alternative splice form of MDM2. (H. A. Steinman et al., 2004, J. Biol. Chem., 279(6):4877-4886). In addition, about 50% of human cancers are observed to have a mutation in or deletion of the TP53 gene. MDM2 is overexpressed in a number of human cancers, including, for example, melanoma, non-small cell lung cancer (NSCLC), breast cancer, esophageal cancer, leukemia, non-Hodgkin's lymphoma and sarcoma. Overexpression of MDM2 has been reported to correlate positively with poor prognosis in individuals having sarcoma, glioma and acute lymphoblastic leukemia (ALL).

Therefore, it is preferable that cancers to be treated in the invention have amplified MDM2 genes or have MDM2 overexpressed in the cancer. In a specific embodiment of the invention, cancers to be treated in the invention can be liposarcoma which have amplified MDM2 genes on the genome of the cancer.

It is also preferable that cancers to be treated in the invention have wild-type TP53 gene on the genome of the cancer. In a specific embodiment of the invention, cancers to be treated in the invention can be liposarcoma (for example, DD or WD liposarcoma) which has wild-type TP53 gene on the genome of the cancer.

In a more specific embodiment of the invention, cancers to be treated in the invention can be liposarcoma which has wild-type TP53 gene and amplified MDM2 genes on the genome of the cancer.

In these specific embodiments, the cancers which have wild-type TP53 gene and/or amplified MDM2 genes on the genome of the cancer can effectively be treated by the administration of the compound of formula (I), which can act as a MDM2 inhibitor.

In an embodiment of the invention, the pharmaceutical composition for use in treating a cancer in a subject in need thereof, comprising the compound of formula (I) or pharmaceutically acceptable salt thereof, wherein the pharmaceutical composition is orally administered to the subject according to a dosage schedule comprising administering to the subject a daily dose of about 80 mg to about 250 mg, more preferably about 100 mg to about 140 mg, about 140 mg to about 180 mg, or about 180 mg to about 250 mg of the compound or salt thereof is provided.

In an embodiment of the invention, the pharmaceutical composition for use in treating a cancer in a subject in need thereof, comprising the compound of formula (II), wherein the pharmaceutical composition is orally administered to the subject according to a dosage schedule comprising administering to the subject a daily dose of about 80 mg to about 250 mg, more preferably about 100 mg to about 140 mg, about 140 mg to about 180 mg, or about 180 mg to about 250 mg of the compound is provided.

In an embodiment of the invention, the present pharmaceutical composition for use in treating a cancer in a subject in need thereof, comprising the compound of formula (II), wherein the pharmaceutical composition is orally administered to the subject according to a dosage schedule comprising administering to the subject a daily dose of about 80 mg to about 250 mg, more preferably about 100 mg to about 140 mg, about 140 mg to about 180 mg, or about 180 mg to about 250 mg of the compound, wherein the cancer is liposarcoma such as DD or WD liposarcoma. Ina specific embodiment, the daily dose is between about 100 mg to about 140 mg, and the cancer is liposarcoma such as DD or WD liposarcoma.

In an embodiment of the invention, the pharmaceutical composition for use in treating a cancer in a subject in need thereof, comprising a therapeutically effective amount of the compound of formula (I) or pharmaceutically acceptable salt thereof, wherein the pharmaceutical composition is orally administered to the subject for at least one cycle of a cyclical dosing schedule, wherein each cycle has a dosing period of at least 10 days, at least 11 days, at least 12 days, at least 13 days, at least 14 days or at least 15 days, in which the compound or salt thereof is administered to the subject daily at a daily dosage of about 80 mg to about 140 mg. In a specific embodiment, the daily dosage is between about 100 mg to about 140 mg. In a specific embodiment of the invention, the dosing period is between about 15 days to about 25 days, more preferably about 21 days. In a specific embodiment of the invention, the dosing period is between about 15 days to about 25 days and the daily dosage is about 100 mg to about 140 mg. In a specific embodiment of the invention, the dosing period is about 21 days and the daily dosage is about 100 mg to about 140 mg, the dosing period is between about 15 days to about 25 days and the daily dosage is about 120 mg, or the dosing period is about 21 days and the daily dosage is about 120 mg.

In an embodiment of the invention, the pharmaceutical composition for use in treating a cancer in a subject in need thereof, comprising a therapeutically effective amount of the compound of formula (I) or pharmaceutically acceptable salt thereof, wherein the pharmaceutical composition is orally administered to the subject for at least one cycle of a cyclical dosing schedule, wherein each cycle has a dosing period of at least 10 days, at least 11 days, at least 12 days, at least 13 days, at least 14 days or at least 15 days, in which the compound or salt thereof is administered to the subject daily at a daily dosage of about 140 mg to about 180 mg. In a specific embodiment of the invention, the dosing period is between about 15 days to about 25 days, more preferably about 21 days. In a specific embodiment of the invention, the dosing period is between about 15 days to about 25 days and the daily dosage is about 140 mg to about 180 mg. In a specific embodiment of the invention, the dosing period is about 21 days and the daily dosage is about 140 mg to about 180 mg, the dosing period is between about 15 days to about 25 days and the daily dosage is about 160 mg, or the dosing period is about 21 days and the daily dosage is about 160 mg.

In an embodiment of the invention, the pharmaceutical composition for use in treating a cancer in a subject in need thereof, comprising a therapeutically effective amount of the compound of formula (I) or pharmaceutically acceptable salt thereof, wherein the pharmaceutical composition is orally administered to the subject for at least one cycle of a cyclical dosing schedule, wherein each cycle has a dosing period of at least 10 days, at least 11 days, at least 12 days, at least 13 days, at least 14 days or at least 15 days, in which the compound or salt thereof is administered to the subject daily at a daily dosage of about 180 mg to about 250 mg. In a specific embodiment of the invention, the dosing period is between about 15 days to about 25 days, more preferably about 21 days. In a specific embodiment of the invention, the dosing period is between about 15 days to about 25 days and the daily dosage is about 180 mg to about 250 mg. In a specific embodiment of the invention, the dosing period is about 21 days and the daily dosage is about 180 mg to about 250 mg, the dosing period is between about 15 days to about 25 days and the daily dosage is about 210 mg, or the dosing period is about 21 days and the daily dosage is about 210 mg.

In an embodiment of the invention, the pharmaceutical composition for use in treating a cancer in a subject in need thereof, comprising a therapeutically effective amount of the compound of formula (I) or pharmaceutically acceptable salt thereof, wherein the pharmaceutical composition is orally administered to the subject for at least one cycle of a cyclical dosing schedule, wherein each cycle has a dosing period of at least 10 days, at least 11 days, at least 12 days, at least 13 days, at least 14 days or at least 15 days, in which the compound or salt thereof is administered to the subject daily at a daily dosage of about 80 mg to about 100 mg. In a specific embodiment of the invention, the dosing period is between about 15 days to about 25 days, more preferably about 21 days. In a specific embodiment of the invention, the dosing period is about 21 days and the daily dosage is about 80 mg to about 100 mg.

In an embodiment of the invention, the pharmaceutical composition for use in treating a cancer in a subject in need thereof, comprising a therapeutically effective amount of the compound of formula (I) or pharmaceutically acceptable salt thereof, wherein the pharmaceutical composition is orally administered to the subject for at least one cycle of a cyclical dosing schedule, wherein each cycle has a dosing period of about 15 days to about 25 days, preferably about 21 days, in which the compound or salt thereof is administered to the subject daily at a daily dosage of about 100 mg to about 140 mg, more preferably about 120 mg, followed by a rest period of about 5 days to about 10 days, preferably about 7 days, in which any of the compound and salt thereof is not administered, is provided.

In an embodiment of the invention, the present pharmaceutical composition for use in treating a cancer in a subject in need thereof, comprising a therapeutically effective amount of the compound of formula (I) or pharmaceutically acceptable salt thereof, wherein the pharmaceutical composition is orally administered for at least one cycle of a cyclical dosing schedule, wherein each cycle has a dosing period of about 21 days, in which the compound or salt thereof is administered to the subject daily at a daily dosage of about 100 mg to about 140 mg, more preferably about 120 mg, followed by a rest period of about 7 days in which any of the compound and salt thereof is not administered, is provided.

In an embodiment of the invention, the pharmaceutical composition for use in treating a cancer in a subject in need thereof, comprising a therapeutically effective amount of the compound of formula (I) or pharmaceutically acceptable salt thereof, wherein the pharmaceutical composition is orally administered to the subject for at least one cycle of a cyclical dosing schedule, wherein each cycle has a dosing period of about 15 days to about 25 days, preferably about 21 days, in which the compound or salt thereof is administered to the subject daily at a daily dosage of about 140 mg to about 180 mg, more preferably about 160 mg, followed by a rest period of about 5 days to about 10 days, preferably about 7 days, in which any of the compound and salt thereof is not administered, is provided.

In an embodiment of the invention, the present pharmaceutical composition for use in treating a cancer in a subject in need thereof, comprising a therapeutically effective amount of the compound of formula (I) or pharmaceutically acceptable salt thereof, wherein the pharmaceutical composition is orally administered for at least one cycle of a cyclical dosing schedule, wherein each cycle has a dosing period of about 21 days, in which the compound or salt thereof is administered to the subject daily at a daily dosage of about 140 mg to about 180 mg, more preferably about 160 mg, followed by a rest period of about 7 days in which any of the compound and salt thereof is not administered, is provided.

In an embodiment of the invention, the pharmaceutical composition for use in treating a cancer in a subject in need thereof, comprising a therapeutically effective amount of the compound of formula (I) or pharmaceutically acceptable salt thereof, wherein the pharmaceutical composition is orally administered to the subject for at least one cycle of a cyclical dosing schedule, wherein each cycle has a dosing period of about 15 days to about 25 days, preferably about 21 days, in which the compound or salt thereof is administered to the subject daily at a daily dosage of about 180 mg to about 250 mg, more preferably about 210 mg, followed by a rest period of about 5 days to about 10 days, preferably about 7 days, in which any of the compound and salt thereof is not administered, is provided.

In an embodiment of the invention, the present pharmaceutical composition for use in treating a cancer in a subject in need thereof, comprising a therapeutically effective amount of the compound of formula (I) or pharmaceutically acceptable salt thereof, wherein the pharmaceutical composition is orally administered for at least one cycle of a cyclical dosing schedule, wherein each cycle has a dosing period of about 21 days, in which the compound or salt thereof is administered to the subject daily at a daily dosage of about 180 mg to about 250 mg, more preferably about 210 mg, followed by a rest period of about 7 days in which any of the compound and salt thereof is not administered, is provided.

In an embodiment of the invention, the pharmaceutical composition for use in treating a cancer in a subject in need thereof, comprising a therapeutically effective amount of the compound of formula (I) or pharmaceutically acceptable salt thereof, wherein the pharmaceutical composition is orally administered to the subject for at least one cycle of a cyclical dosing schedule, wherein each cycle has a dosing period of about 15 days to about 25 days, preferably about 21 days, in which the compound or salt thereof is administered to the subject daily at a daily dosage of about 80 mg to about 100 mg, more preferably about 90 mg, followed by a rest period of about 5 days to about 10 days, preferably about 7 days, in which any of the compound and salt thereof is not administered, is provided.

In an embodiment of the invention, the present pharmaceutical composition for use in treating a cancer in a subject in need thereof, comprising a therapeutically effective amount of the compound of formula (I) or pharmaceutically acceptable salt thereof, wherein the pharmaceutical composition is orally administered for at least one cycle of a cyclical dosing schedule, wherein each cycle has a dosing period of about 21 days, in which the compound or salt thereof is administered to the subject daily at a daily dosage of about 80 mg to about 100 mg, more preferably about 90 mg, followed by a rest period of about 7 days in which any of the compound and salt thereof is not administered, is provided.

In an embodiment of the invention, the present pharmaceutical composition for use in treating a cancer in a subject in need thereof, comprising a therapeutically effective amount of the compound of formula (II), wherein the pharmaceutical composition is orally administered to the subject for at least one cycle of a cyclical dosing schedule, wherein each cycle has a dosing period of about 15 days to about 25 days, preferably about 21 days, in which the compound is administered daily at a daily dosage of about 80 mg to about 140 mg, preferably about 100 mg to about 140 mg, more preferably about 120 mg, followed by a rest period of about 5 days to about 10 days, preferably about 7 days, in which the compound is not administered, is provided. In a specific embodiment of the invention, the daily dosage is between about 100 mg to about 140 mg, the dosing period is between about 15 days to about 25 days, and the rest period is between about 5 days to about 10 days. In another specific embodiment of the invention, the daily dosage is about 120 mg, the dosing period is between about 15 days to about 25 days, and the rest period is between about 5 days to about 10 days. In another specific embodiment of the invention, the daily dosage is between about 100 mg to about 140 mg, the dosing period is about 21 days, and the rest period is about 7 days. In another specific embodiment of the invention, the daily dosage is about 120 mg, the dosing period is about 21 days, and the rest period is about 7 days.

In an embodiment of the invention, the present pharmaceutical composition for use in treating a cancer in a subject in need thereof, comprising a therapeutically effective amount of the compound of formula (II), wherein the pharmaceutical composition is orally administered to the subject for at least one cycle of a cyclical dosing schedule, wherein each cycle has a dosing period of about 15 days to about 25 days, preferably about 21 days, in which the compound is administered daily at a daily dosage of about 140 mg to about 180 mg, more preferably about 160 mg, followed by a rest period of about 5 days to about 10 days, preferably about 7 days, in which the compound is not administered, is provided. In a specific embodiment of the invention, the daily dosage is between about 140 mg to about 180 mg, the dosing period is between about 15 days to about 25 days, and the rest period is between about 5 days to about 10 days. In another specific embodiment of the invention, the daily dosage is about 160 mg, the dosing period is between about 15 days to about 25 days, and the rest period is between about 5 days to about 10 days. In another specific embodiment of the invention, the daily dosage is between about 140 mg to about 180 mg, the dosing period is about 21 days, and the rest period is about 7 days. In another specific embodiment of the invention, the daily dosage is about 160 mg, the dosing period is about 21 days, and the rest period is about 7 days.

In an embodiment of the invention, the present pharmaceutical composition for use in treating a cancer in a subject in need thereof, comprising a therapeutically effective amount of the compound of formula (II), wherein the pharmaceutical composition is orally administered to the subject for at least one cycle of a cyclical dosing schedule, wherein each cycle has a dosing period of about 15 days to about 25 days, preferably about 21 days, in which the compound is administered daily at a daily dosage of about 180 mg to about 250 mg, more preferably about 210 mg, followed by a rest period of about 5 days to about 10 days, preferably about 7 days, in which the compound is not administered, is provided. In a specific embodiment of the invention, the daily dosage is between about 180 mg to about 250 mg, the dosing period is between about 15 days to about 25 days, and the rest period is between about 5 days to about 10 days. In another specific embodiment of the invention, the daily dosage is about 210 mg, the dosing period is between about 15 days to about 25 days, and the rest period is between about 5 days to about 10 days. In another specific embodiment of the invention, the daily dosage is between about 180 mg to about 250 mg, the dosing period is about 21 days, and the rest period is about 7 days. In another specific embodiment of the invention, the daily dosage is about 180 mg, the dosing period is about 21 days, and the rest period is about 7 days.

In an embodiment of the invention, the present pharmaceutical composition for use in treating a cancer in a subject in need thereof, comprising a therapeutically effective amount of the compound of formula (II), wherein the pharmaceutical composition is orally administered for at least one cycle of a cyclical dosing schedule, wherein each cycle has a dosing period of about 15 days to about 25 days, preferably about 21 days, in which the compound or salt thereof is administered daily at a daily dosage of about 80 mg to about 140 mg, preferably about 100 mg to about 140 mg, more preferably about 120 mg, followed by a rest period of about 5 days to about 10 days, preferably about 7 days, in which the compound is not administered, wherein the cancer is liposarcoma such as DD or WD liposarcoma is provided. In a specific embodiment of the invention, the daily dosage is between about 100 mg to about 140 mg, the dosing period is between about 15 days to about 25 days, and the rest period is between about 5 days to about 10 days. In another specific embodiment of the invention, the daily dosage is about 120 mg, the dosing period is between about 15 days to about 25 days, and the rest period is between about 5 days to about 10 days. In another specific embodiment of the invention, the daily dosage is between about 100 mg to about 140 mg, the dosing period is about 21 days, and the rest period is about 7 days. In another specific embodiment of the invention, the daily dosage is about 120 mg, the dosing period is about 21 days, and the rest period is about 7 days.

In an embodiment of the invention, the present pharmaceutical composition for use in treating a cancer in a subject in need thereof, comprising a therapeutically effective amount of the compound of formula (II), wherein the pharmaceutical composition is orally administered for at least one cycle of a cyclical dosing schedule, wherein each cycle has a dosing period of about 15 days to about 25 days, preferably about 21 days, in which the compound or salt thereof is administered daily at a daily dosage of about 140 mg to about 180 mg, more preferably about 160 mg, followed by a rest period of about 5 days to about 10 days, preferably about 7 days, in which the compound is not administered, wherein the cancer is liposarcoma, for example, DD or WD liposarcoma is provided. In a specific embodiment of the invention, the daily dosage is between about 140 mg to about 180 mg, the dosing period is between about 15 days to about 25 days, and the rest period is between about 5 days to about 10 days. In another specific embodiment of the invention, the daily dosage is about 160 mg, the dosing period is between about 15 days to about 25 days, and the rest period is between about 5 days to about 10 days. In another specific embodiment of the invention, the daily dosage is between about 140 mg to about 180 mg, the dosing period is about 21 days, and the rest period is about 7 days. In another specific embodiment of the invention, the daily dosage is about 160 mg, the dosing period is about 21 days, and the rest period is about 7 days.

In an embodiment of the invention, the present pharmaceutical composition for use in treating a cancer in a subject in need thereof, comprising a therapeutically effective amount of the compound of formula (II), wherein the pharmaceutical composition is orally administered for at least one cycle of a cyclical dosing schedule, wherein each cycle has a dosing period of about 15 days to about 25 days, preferably about 21 days, in which the compound or salt thereof is administered daily at a daily dosage of about 180 mg to about 250 mg, more preferably about 210 mg, followed by a rest period of about 5 days to about 10 days, preferably about 7 days, in which the compound is not administered, wherein the cancer is liposarcoma such as DD or WD liposarcoma is provided. In a specific embodiment of the invention, the daily dosage is between about 180 mg to about 250 mg, the dosing period is between about 15 days to about 25 days, and the rest period is between about 5 days to about 10 days. In another specific embodiment of the invention, the daily dosage is about 210 mg, the dosing period is between about 15 days to about 25 days, and the rest period is between about 5 days to about 10 days. In another specific embodiment of the invention, the daily dosage is between about 180 mg to about 250 mg, the dosing period is about 21 days, and the rest period is about 7 days. In another specific embodiment of the invention, the daily dosage is about 210 mg, the dosing period is about 21 days, and the rest period is about 7 days.

In an embodiment of the invention, the present pharmaceutical composition for use in treating a cancer in a subject in need thereof, comprising a therapeutically effective amount of the compound of formula (II), wherein the pharmaceutical composition is orally administered to the subject for at least one cycle of a cyclical dosing schedule, wherein each cycle has a dosing period of about 15 days to about 25 days, preferably about 21 days, in which the compound or salt thereof is administered daily at a daily dosage of about 80 mg to about 100 mg, more preferably 90 mg, of the compound, followed by a rest period of about 5 days to about 10 days, preferably about 7 days, in which the compound is not administered, is provided. In a specific embodiment of the invention, the daily dosage is about 90 mg, the dosing period is between about 15 days to about 25 days, and the rest period is between about 5 days to about 10 days. In another specific embodiment of the invention, the daily dosage is between about 80 mg to about 100 mg, the dosing period is about 21 days, and the rest period is about 7 days. In another specific embodiment of the invention, the daily dosage is about 90 mg, the dosing period is about 21 days, and the rest period is about 7 days.

In an embodiment of the invention, the present pharmaceutical composition for use in treating a cancer in a subject in need thereof, comprising a therapeutically effective amount of the compound of formula (II), wherein the pharmaceutical composition is orally administered for at least one cycle of a cyclical dosing schedule, wherein each cycle has a dosing period of about 15 days to about 25 days, preferably about 21 days, in which the compound or salt thereof is administered daily at a daily dosage of about 80 mg to about 100 mg of the compound, followed by a rest period of about 5 days to about 10 days, preferably about 7 days, in which the compound is not administered, wherein the cancer is liposarcoma such as DD or WD liposarcoma is provided. In a specific embodiment of the invention, the daily dosage is about 90 mg, the dosing period is between about 15 days to about 25 days, and the rest period is between about 5 days to about 10 days. In another specific embodiment of the invention, the daily dosage is between about 80 mg to about 100 mg, the dosing period is about 21 days, and the rest period is about 7 days. In another specific embodiment of the invention, the daily dosage is about 90 mg, the dosing period is about 21 days, and the rest period is about 7 days.

In an embodiment of the invention, the pharmaceutical composition may comprise a pharmaceutically acceptable excipient (for example, vehicles, adjuvants and additives such as bulking agent, viscosity-increasing agent, adhesive, plasticizer, binder, disintegrant, tablet lubricant, glidant, coating agent, antioxidant, preservative, humectant, opacifying agent, polishing agent, sweetening agent, aroma, flavors, and colorant) and can be prepared as a pharmaceutical composition for oral administration.

The pharmaceutical composition of the invention can be formulated by the ordinary skill in the art. The pharmaceutical composition for oral administration can be tablets, powders, granules, capsules, pills, troches, solutions, syrups, elixirs, emulsions, and oily or aqueous suspension. Pharmaceutical solutions can be made by forming acid addition salt using a pharmaceutically acceptable acid such as p-toluenesulfonate.

The compound of formula (I) or (II) can be easily prepared by those skilled in the art according to Example 70 of WO2012/121361 and Example 7 of WO2014/038606, which patent documents are incorporated by reference herein in its entirety. The compound of formula (II) may be prepared in a form of crystal.

In another aspect of the invention, a method for treating a cancer in a subject in need thereof, comprising orally and daily administering to the subject a therapeutically effective amount of the compound of formula (I) or pharmaceutically acceptable salt thereof according to a dosage schedule, wherein the dosage schedule comprises administering a daily dose of about 80 mg to about 250 mg of the compound or salt thereof to the subject. In a preferable embodiment of the dosage schedule, a daily dose of the compound or salt thereof is preferably between about 100 mg to about 140 mg, and more preferably about 120 mg. In a preferable embodiment of the dosage schedule, a daily dose of the compound or salt thereof is preferably between about 140 mg to about 180 mg, and more preferably about 160 mg. In a preferable embodiment of the dosage schedule, a daily dose of the compound or salt thereof is preferably between about 180 mg to about 250 mg, and more preferably about 210 mg. In a preferable embodiment of the dosage schedule, a daily dose of the compound or salt thereof is preferably between about 80 mg to about 100 mg, and more preferably about 90 mg. In a preferable embodiment, a cancer to be treated can be liposarcoma, especially a liposarcoma having amplified MDM2 genes in the genome of the liposarcoma. In a preferable embodiment, a pharmaceutically acceptable salt of the compound of formula (I) can be the compound of formula (II).

In an embodiment of the invention, a method for treating a cancer in a subject in need thereof, comprising orally and daily administering a therapeutically effective amount of the compound of formula (I) or pharmaceutically acceptable salt thereof for at least one cycle of a cyclical dosing schedule, wherein each cycle has a dosing period of 15 to 25 days, in which the compound or salt thereof is administered daily at a daily dosage of about 80 mg to about 250 mg of the compound or salt thereof, followed by a rest period of 5 to 10 days in which any of the compound and salt thereof is not administered. In a preferable embodiment of the dosage schedule, a daily dose of the compound or salt thereof is preferably between about 100 mg to about 140 mg, and more preferably about 120 mg. In a preferable embodiment of the dosage schedule, a daily dose of the compound or salt thereof is preferably between about 140 mg to about 180 mg, and more preferably about 160 mg. In a preferable embodiment of the dosage schedule, a daily dose of the compound or salt thereof is preferably between about 180 mg to about 250 mg, and more preferably about 210 mg. In a preferable embodiment, a cancer to be treated can be liposarcoma, especially a liposarcoma having amplified MDM2 genes in the genome of the liposarcoma. In a preferable embodiment, a pharmaceutically acceptable salt of the compound of formula (I) can be the compound of formula (II).

The compound of formula (I) or (II) may be used in combination with additional anti-tumor agent(s). The compound of formula (I) or (II) may be used in combination with additional anti-tumor agent(s). Examples thereof include anti-tumor antibiotics, anti-tumor plant constituents, BRMs (biological response modifiers), hormones, vitamins, anti-tumor antibodies, molecular target drugs, and other anti-tumor agents. In an preferred embodiment of the invention, anti-tumor agents to be used in combination with the compound of formula (I) or (II) may be or may not be an MDM2 inhibitor.

More specifically, examples of alkylating agents include the following: alkylating agents such as nitrogen mustard, nitrogen mustard N-oxide, bendamustine and chlorambucil; amidine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin, and ranimustine; and busulfan, improsulfan tosylate, and dacarbazine.

Examples of various metabolic antagonists include the following: purine metabolic antagonists such as 6-mercaptopurine, 6-thioguanine, and thioinosine; pyrimidine metabolic antagonists such as fluorouracil, tegafur, tegafur-uracil, carmofur, doxifluridine, broxuridine, cytarabine, and enocitabine; and folic acid metabolic antagonists such as methotrexate and trimetrexate.

Examples of anti-tumor antibiotics include mitomycin C, bleomycin, peplomycin, daunorubicin, aclarubicin, doxorubicin, idarubicin, pirarubicin, THP-adriamycin, 4'-epidoxorubicin, and epirubicin; and chromomycin A3 and actinomycin D.

Examples of anti-tumor plant constituents and their derivatives include the following: vinca alkaloids such as vindesine, vincristine, and vinblastine; taxanes such as paclitaxel, docetaxel, and cabazitaxel; and epipodophyllotoxins such as etoposide and teniposide.

Examples of BRMs include tumor necrosis factors and indomethacin.

Examples of hormones include hydrocortisone, dexamethasone, methylprednisolone, prednisolone, prasterone, betamethasone, triamcinolone, oxymetholone, nandrolone, metenolone, fosfestrol, ethinylestradiol, chlormadinone, medroxyprogesterone, and mepitiostane.

Examples of vitamins include vitamin C and vitamin A.

Examples of anti-tumor antibodies and molecular target drugs include trastuzumab, rituximab, cetuximab, nimotuzumab, denosumab, bevacizumab, infliximab, ipilimumab, nivolumab, pembrolizumab, avelumab, pidilizumab, atezolizumab, ramucirumab imatinib mesilate, dasatinib, gefitinib, erlotinib, sunitinib, lapatinib, vemurafenib, dabrafenib, trametinib, pazopanib, palbociclib, panobinostat, sorafenib, ibrutinib, bortezomib, carfilzomib, ixazomib, and quizartinib.

Examples of other anti-tumor agents include cisplatin, carboplatin, oxaliplatin, tamoxifen, letrozole, anastrozole, exemestane, toremifene citrate, fulvestrant, bicalutamide, flutamide, mitotane, leuprorelin, goserelin acetate, camptothecin, ifosfamide, cyclophosphamide, melphalan, L-asparaginase, aceglatone, sizofuran, picibanil, procarbazine, pipobroman, neocarzinostatin, hydroxyurea, ubenimex, azacytidine, decitabine, thalidomide, lenalidomide, pomalidomide, eribulin, tretinoin, and krestin.

Hereinafter, the following examples are provided only for illustrative purposes and it is understood that the invention is not limited the examples.

EXAMPLES

Example 1

This Example describes the clinical study wherein the specific dosage regimen for the test compound (also referred to as "Compound 2") shown unexpectedly good results in treating cancers.

Test Compound
(3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide mono(4-methylbenzenesulfonate) monohydrate (Compound 2) was prepared as described in WO2012/121361 and WO2014/038606, which are incorporated by reference herein in its entirety.

Subject Eligibility Criteria
Inclusion Criteria for Solid Tumor/Lymphoma Subject:
1. Has a histologically or cytologically documented advanced solid tumor or lymphoma that has relapsed from or is refractory to standard treatment, or for which no standard treatment is available.
2. Man or woman≥18 years old.
3. Has an Eastern Cooperative Oncology Group (ECOG) performance status 0-1.
4. Has adequate bone marrow function, adequate renal function, adequate hepatic function, and adequate blood clotting function.

The demographic/characteristics of the subjects enrolled in the dose escalation part of the study were as summarized in Table 1.

TABLE 1

| Subject Demographics and Baseline | |
|---|---|
| Demographic/Characteristics Statistic/Category | Total (N = 34) |
| Age at Informed Consent (years) | |
| Median | 59.5 |
| Minimum | 42 |
| Maximum | 79 |
| Gender (n, %) | |
| Male | 15 (44.1) |
| Female | 19 (55.9) |
| Number of Prior Regimens | |
| Median | 3.00 |
| Minimum | 0.0 |
| Maximum | 11.0 |
| Cancer Type (n, %) | |
| Liposarcoma | 15 (44.1) |
| Melanoma | 4 (11.8) |
| Neuroendocrine | 2 (5.9) |
| Lymphoma | 2 (5.9) |
| Adenoid cystic | 2 (5.9) |
| Leiomyosarcoma | 2 (5.9) |
| Colorectal | 1 (2.9) |
| Renal | 1 (2.9) |
| Lung | 1 (2.9) |
| Chordoma | 1 (2.9) |
| Salivary adenocarcinoma | 1 (2.9) |
| Adrenocortical carcinoma | 1 (2.9) |
| Maxillary sinus adenocarcinoma | 1 (2.9) |
| TP53 Genotyping (n, %) | |
| Wild type | 26 (76.5) |
| Mutant | 6 (17.6) |
| Not available | 2 (5.9) |

Dosage regimen Compound 2 was administered as an oral capsule comprising a pharmaceutically acceptable carrier (diluting agent, plasticizer, disintegrator and lubricant). Compound 2 was administered to the subjects once daily on Days 1 to 21 of a 28-day cycle (QD21/28). An alternative drug administration schedule was considered after establishing the maximum tolerated dose (MTD) of Compound 2 in solid tumor and/or lymphoma subjects using the above schedule, and upon review of the human safety. Subjects were administered Compound 2 in fasting conditions by avoiding food for 2 hours before and 1 hour after drug administration. Dose-escalation of Compound 2 to determine the MTD was guided by the modified continuous reassessment method (mCRM) using a Bayesian logistic regression model (BLRM) following escalation with overdose control (EWOC) principle. Dose escalation began in subjects with advanced solid tumors or lymphomas with a starting dose of Compound 2 at 15 mg/day based on the Highest Non-Severely Toxic Dose (HNSTD) of 3 mg/kg in dogs.

Dose Limiting Toxicity Definition A DLT was defined as any treatment-emergent adverse event (TEAE) not attributable to disease or disease-related processes that occurred during the observation period (Cycle 1) in each dose-level cohort and was grade 3 or higher according to NCI CTCAE, version 4. Subjects who were unable to complete at least 75% of the prescribed doses (i.e., 16 days) of Compound 2 in the first 21 days as a result of nondisease-related≥grade 2 adverse event (AE) were considered to have a DLT.

Tumor assessment Tumor assessment was performed at baseline, within every 2 cycles while the subject remained on study for the first 9 cycles and then every 3 cycles thereafter (start of Cycles 3, 5, 7, and 9, then Cycles 12, 15, etc.).

Tumor rebiopsy To search for possible mechanisms of acquired resistance to Compound 2, an optional tumor rebiopsy was performed within 30 days following the last dose of Compound 2 treatment for subjects who had achieved an initial complete response/partial response by standard response criteria but later developed progressive disease while on therapy, preferably prior to initiating new therapy.

TP53 Genotyping, Subject Enrollment and Early Discontinuation Option

Tumor TP53 genotyping was performed using archived formalin-fixed paraffin-embedded (FFPE) or frozen samples in all enrolled subjects. Confirmation of TP53 wildtype status was not required prior to Compound 2 dosing. During the study, in the event when a subject was found to contain a nonsynonymous mutation, insertion or deletion in the TP53 gene after Compound 2 had begun, the investigator and subject was informed about the genotyping result and given the option to discontinue study drug early.

Study Duration The number of treatment cycles was not fixed in this study. Subjects, who continued to derive clinical benefit from treatment in the absence of withdrawal of subject consent, progression, or unacceptable toxicity, continued treatment at the physicians' discretion. Continuing treatment was given in a separate extension phase of the protocol and data collected from those patients were captured in a separate database.

Treatment Arms In this open-label, single-arm, dose escalation study, each subject received Compound 2 orally once daily on Days 1 to 21 of a 28-day cycle.

Safety Parameters The safety profile was based on AEs, physical examination findings, vital sign measurements, clinical laboratory measurements, and ECG recordings. All subjects receiving at least 1 dose of Compound 2 were included in the safety analyses.

Tumor Response Response assessment was performed according to the Schedule of Events or if disease progression was suspected. Radiographic assessment included computerized tomography (CT) of all affected sites. In addition, subjects with lymphoma underwent a ($^{18}$F) fluorodeoxyglucose-positron emission tomography FDG-PET scan. Tumor responses were assessed by the physicians according to RECIST 1.1 criteria for subjects with solid tumors and revised IWG criteria for subjects with lymphoma. Descriptive statistics for the greatest percent change in the sum of longest dimensions (SLD) of measurable tumors were provided. A waterfall plot of the greatest percent change from screening in the SLD for each subject was presented for subjects with advanced solid malignancies and lymphomas. In addition, descriptive statistics for FDG-PET scans were provided for lymphoma subjects according to revised IWG criteria.

Results 34 subjects were enrolled in the dose escalation part of the phase 1 study, 31 of which were evaluable for dose limiting toxicities (DLT). The subjects ranged in age between 42 years and 79 years, with a median age of 59.5 years. Subjects with thirteen different tumors types, of which 76.5% were TP53 wild-type, were enrolled in the study, with liposarcoma subjects being the most frequent (n=15; 44.1%). The drug was studied at 7 increasing dose levels starting from 15 mg through 30, 60, 120 and 160 mg to the highest tested dose of 240 mg in a QD schedule in 21 days out of 28 day cycles (QD 21/28). A 90 mg dose in an alternate schedule of everyday administration in 28 ay cycles (QD 28/28) was also tested. The maximum tolerated dose (MTD) was determined to be 120 mg with 2 DLTs out of 13 subjects in the QD 21/28 schedule. The 90 mg in QD 28/28 schedule was also determined to be an MTD in this dosing schedule with one out of 9 subjects experiencing a DLT.

Figure 2:
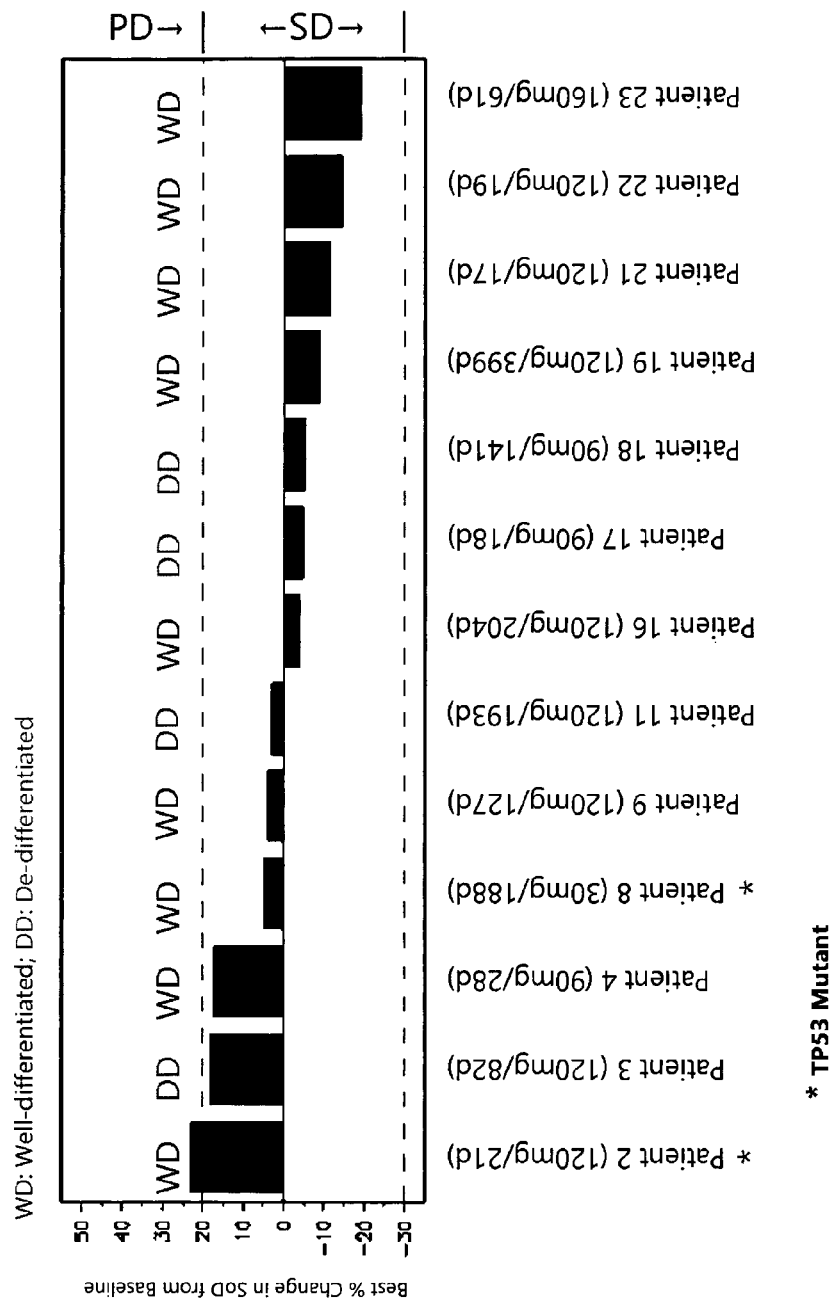

Twenty three subjects were evaluable for efficacy based on RECIST v1.1 in this study. Most subjects (21 out of 23) experienced stable disease (SD) as the best tumor response with >10% tumor shrinkage in 3 subjects (FIG. 1). Durable stable disease was seen for many subjects with the median progression free survival (PFS) for the overall population at 5.72 months. Interestingly, the greatest tumor shrinkage and most durable stable disease were seen in subjects with well-differentiated or de-differentiated (WD/DD) liposarcoma (Table 2, FIG. 2). The 3- and 6-month PFS rate in the liposarcoma subjects were 91.7% and 76.4%, respectively (Table 2). Further attention should be drawn to the result that the 12-month PFS rate in the liposarcoma subjects was 57.3% (Table 2). The European Organization of Research and Treatment of Cancer (EORTC) has defined the criterion for an active agent in second line soft tissue sarcoma as one with a 12-week PFS>40%. Thus, our efficacy results in liposarcoma compare favorably to historical data.

TABLE 2

Evaluation of Progression Free survival for the study populations
Progression Free Survival
Part 1 (Dose Escalation)
Full Analysis Set

|  | Liposarcoma (N = 13) | Non-Liposarcoma (N = 14) | Overall (N = 27) |
| --- | --- | --- | --- |
| Subjects with Events (n, %) | 3 (23.1) | 9 (64.3) | 12 (44.4) |
| Subjects without Events (Censored) (n, %) | 10 (76.9) | 5 (35.7) | 15 (55.6) |
| Progression-Free Survival (months)* |  |  |  |
| Median (95% CI) | — | 4.04 (1.68, 8.57) | 5.72 (4.04, –) |
| Log-Rank p-value (Liposarcoma vs. Non-Liposarcoma) | 0.0394 |  |  |
| Rate (%) of Being Alive Without Progresion at Least * |  |  |  |
| 3 months (95% CI) | 91.7 (53.9, 98.8) | 58.4 (26.2, 80.6) | 74.5 (51.4, 87.8) |
| 6 months (95% CI) | 76.4 (30.9, 94.0) | 23.4 (3.8, 32.5) | 47.4 (22.5, 68.6) |

TABLE 2-continued

Evaluation of Progression Free survival for the study populations
Progression Free Survival
Part 1 (Dose Escalation)
Full Analysis Set

|  | Liposarcoma (N = 13) | Non-Liposarcoma (N = 14) | Overall (N = 27) |
|---|---|---|---|
| 9 months (95% CI) | 57.3 (14.6, 85.1) | 11.7 (0.7, 39.9) | 29.7 (8.7, 54.5) |
| 12 months (95% CI) | 57.3 (14.6, 85.1) | 11.7 (0.7, 39.9) | 29.7 (8.7, 54.5) |

*Kaplan-Meier estimate.
— = not estimable (i.e., median PFS has not been reached).

Treatment emergent adverse events (TEAE) of any grade at any treatment cycle irrespective of causality were observed in 97.1% of the subjects, 55.9% of which were grade 3 or higher in severity. The most common TEAEs irrespective of causality were neutropenia (17.6%), thrombocytopenia (32.4%), anemia (38.2%), nausea (64.7%), vomiting (35.3%), diarrhea (35.3%), constipation (23.5), decreased appetite (50.0%), dysgeusia (20.6%), fatigue (52.9%), dyspnoea (26.5%), hypoalbuminemia (32.4%), peripheral edema (17.6%) and hyperglycemia (29.4%). The most common drug-related TEAEs were hematological (thrombocytopenia, anemia, neutropenia), gastrointestinal (nausea, vomiting and diarrhea), and fatigue, consistent with on-target toxic effects of MDM2 inhibitors [Lillian L. Siu, et al, J Clin Oncol 32:5s, 2014 (suppl; abstr 2535) and Isabelle Ray-Coquard, et al, The Lancet Oncology, 13(11):1133-1140 (November 2012)]. Prolonged thrombocytopenia resulting in more than 4 weeks dose interruption or discontinuation was seen in 8 subjects, 2 were treated at the MTD of 120 mg QD 21/28. Nine out of 13 subjects at 120 mg QD 21/28 and 6 out of 9 subjects at 90 mg QD 28/28 (MTD at the two dosing schedules) experienced Common Terminology Criteria for Adverse Events (CTCAE) v4.0 grade≥3 TEAEs, thrombocytopenia being the most predominant (Table 3). A total of 6 subjects experienced DLTs, all of which were at MTD or higher doses (Table 4). All the 3 DLTs at the MTD arose due to thrombocytopenia that resulted in >1 week delay in starting cycle 2. The patients with hematological malignancies tolerated 160 mg.

TABLE 3

Incidence of CTCAE v4.0 Grade ≥3 TEAEs at MTD
(120 mg QD 21/28 and 90 mg QD 28/28)

| MTD Dose | Subject | Adverse Event | DLT |
|---|---|---|---|
| 120 mg QD 21/28 | Patient 5 | Anemia | No |
| | Patient 11 | Vomiting, Nausea, Hypokalemia, Thrombocytopenia | No |
| | Patient 24 | Thrombocytopenia, shortness of breath | Yes |
| | Patient 21 | Thrombocytopenia | No |
| | Patient 19 | Pulmonary Embolism | No |
| | Patient 12 | Thrombocytopenia | No |
| | Patient 16 | Fatigue, Hypotension | No |
| | Patient 9 | Fatigue, Hypotension, Thrombocytopenia, Anemia | No |
| | Patient 22 | Leucopenia, Thrombocytopenia, Neutropenia | No |
| 90 mg QD 28/28 | Patient 4 | Thrombocytopenia, Hypokalemia | Yes |
| | Patient 25 | Thrombocytopenia | No |
| | Patient 10 | Neutropenia | No |
| | Patient 26 | Lymphocyte count decreased | No |
| | Patient 18 | Leucopenia, Neutropenia, Thrombocytopenia, Anemia, Lymphocytopenia | No |
| | Patient 20 | Thrombocytopenia | No |

TABLE 4

Dose liming toxicities experienced by the subjects and their corresponding doses, grades and actions taken

| Dose (Schedule) | Subject | Adverse Event | CTCAE Grade | SAE | Action Taken |
|---|---|---|---|---|---|
| 90 mg (QD 28/28) | Patient 4 | Thrombocytopenia | 3* | No | Drug Withdrawn (due to disease progression) |
| 120 mg (QD 21/28) | Patient 21 | Thrombocytopenia | 2* | No | Drug Interrupted |
| | Patient 24 | Thrombocytopenia | 3* | No | Drug Interrupted |
| 160 mg (QD 21/28) | Patient 27 | Anorexia | 3 | No | Drug Interrupted |
| | | Nausea | 3 | No | |
| | | Vomiting | 3 | No | |
| | Patient 23 | Neutropenia | 4 | No | Drug Interrupted and Dose Reduced |
| | | Thrombocytopenia | 2 | No | |
| 240 mg (QD 21/28) | Patient 28 | Thrombocytopenia | 4 | Yes | Dose Reduced |
| | | Febrile Neutropenia | 4 | Yes | Dose Reduced |

*A delay of ≥1 week in initiating Cycle 2 secondary to a non disease-related ≥ grade 2 adverse event will be considered a DLT.

The invention claimed is:

1. A method of treating a liposarcoma in a subject in need thereof, comprising orally administering to a subject a daily dose of about 80 mg to about 250 mg of a compound of formula (I) or a pharmaceutically acceptable salt thereof

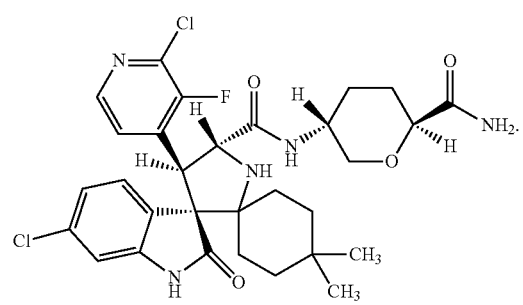

(I)

2. The method of claim 1, wherein the daily dose is about 80 mg to about 140 mg of the compound or the salt thereof.
3. The method of claim 1, wherein the daily dose is about 80 mg to about 100 mg of the compound or the salt thereof.
4. The method of claim 1, wherein the daily dose is about 90 mg of the compound or the salt thereof.

5. The method of claim 1, wherein the daily dose is about 100 mg to about 140 mg of the compound or the salt thereof.

6. The method of claim 1, wherein the daily dose is about 120 mg of the compound or the salt thereof.

7. The method of claim 1, wherein the liposarcoma has amplified MDM2 genes in its genome or overexpresses MDM2.

8. The method of claim 1, wherein the salt thereof is a p-toluenesulfonic acid salt monohydrate of formula (II)

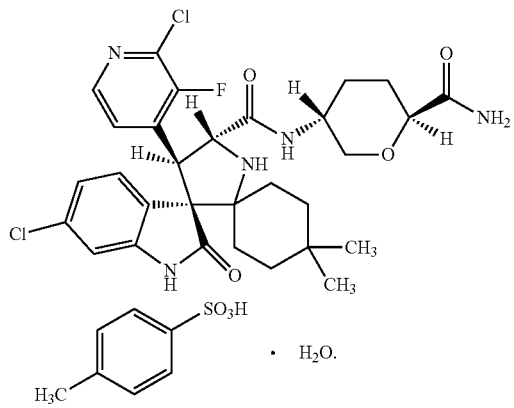

9. A method of treating a liposarcoma in a subject in need thereof, comprising orally administering to a subject a daily dosage of about 80 mg to about 250 mg of a compound of formula (I) or a pharmaceutically acceptable salt thereof for at least one cycle of a cyclical dosing schedule comprising a dosing period of at least 10 days

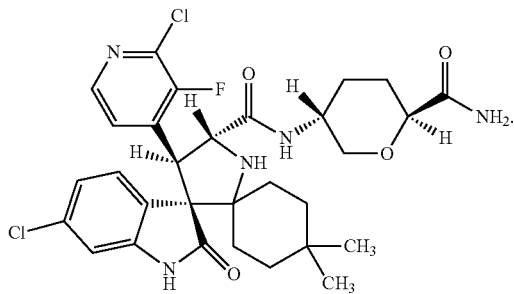

10. The method of claim 9, wherein the daily dosage is about 80 mg to about 140 mg of the compound or the salt thereof.

11. The method of claim 9, wherein the daily dosage is about 80 mg to about 100 mg of the compound or the salt thereof.

12. The method of claim 9, wherein the daily dosage is about 90 mg of the compound or the salt thereof.

13. The method of claim 9, wherein the daily dosage is about 100 mg to about 140 mg of the compound or the salt thereof.

14. The method of claim 9, wherein the daily dosage is about 120 mg of the compound or the salt thereof.

15. The method of claim 9, wherein the daily dosage is about 140 mg to about 180 mg of the compound or the salt thereof.

16. The method of claim 9, wherein the daily dosage is about 160 mg of the compound or the salt thereof.

17. The method of claim 9, wherein the daily dosage is about 180 mg to about 250 mg of the compound or the salt thereof.

18. The method of claim 9, wherein the daily dosage is about 210 mg of the compound or the salt thereof.

19. The method of claim 9, wherein each cycle of the cyclical dosing schedule is followed by a rest period in which the compound or the salt thereof is not administered to the subject.

20. The method of claim 19, where the rest period is about 5 to about 10 days.

21. The method of claim 9, wherein each cycle of the cyclical dosing schedule comprises a dosing period of about 15 days to about 25 days, wherein the compound or the salt thereof is administered at a daily dosage of about 100 mg to about 140 mg, followed by a rest period of about 5 days to about 10 days, wherein the compound or the salt thereof is not administered.

22. The method of claim 9, wherein each cycle of the cyclical dosing schedule comprises a dosing period of about 15 days to about 25 days, wherein the compound or the salt thereof is administered at a daily dosage of about 120 mg, followed by a rest period of about 5 days to about 10 days, wherein the compound or the salt thereof is not administered.

23. The method of claim 9, wherein each cycle of the cyclical dosing schedule comprises a dosing period of about 15 days to about 25 days, wherein the compound or the salt thereof is administered at a daily dosage of about 140 mg to about 180 mg, followed by a rest period of about 5 days to about 10 days, wherein the compound or the salt thereof is not administered.

24. The method of claim 9, wherein each cycle of the cyclical dosing schedule comprises a dosing period of about 15 days to about 25 days, wherein the compound or the salt thereof is administered at a daily dosage of about 160 mg, followed by a rest period of about 5 days to about 10 days, wherein the compound or the salt thereof is not administered.

25. The method of claim 9, wherein each cycle of the cyclical dosing schedule comprises a dosing period of about 15 days to about 25 days, wherein the compound or the salt thereof is administered at a daily dosage of about 180 mg to about 250 mg, followed by a rest period of about 5 days to about 10 days, wherein the compound or the salt thereof is not administered.

26. The method of claim 9, wherein each cycle of the cyclical dosing schedule comprises a dosing period of about 15 days to about 25 days, wherein the compound or the salt thereof is administered at a daily dosage of about 210 mg, followed by a rest period of about 5 days to about 10 days, wherein the compound or the salt thereof is not administered.

27. The method of claim 9, wherein each cycle of the cyclical dosing schedule comprises a dosing period of about 21 days, wherein the compound or the salt thereof is administered at a daily dosage of about 100 mg to about 140 mg, followed by a rest period of about 7 days, wherein the compound or the salt thereof is not administered.

28. The method of claim 9, wherein each cycle of the cyclical dosing schedule comprises a dosing period of about 21 days, wherein the compound or the salt thereof is administered at a daily dosage of about 140 mg to about 180 mg, followed by a rest period of about 7 days, wherein the compound or the salt thereof is not administered.

29. The method of claim 9, wherein each cycle of the cyclical dosing schedule comprises a dosing period of about 21 days, wherein the compound or the salt thereof is administered at a daily dosage of about 180 mg to about 250 mg, followed by a rest period of about 7 days, wherein the compound or the salt thereof is not administered.

30. The method of claim 9, wherein each cycle of the cyclical dosing schedule comprises a dosing period of about 15 days to about 25 days, wherein the compound or the salt thereof is administered at a daily dosage of about 80 mg to about 100 mg, followed by a rest period of about 5 days to about 10 days, wherein the compound or the salt thereof is not administered.

31. The method of claim 9, wherein each cycle of the cyclical dosing schedule comprises a dosing period of about 15 days to about 25 days, wherein the compound or the salt thereof is administered at a daily dosage of about 90 mg, followed by a rest period of about 5 days to about 10 days, wherein the compound or the salt thereof is not administered.

32. The method of claim 9, wherein each cycle of the cyclical dosing schedule comprises a dosing period of about 21 days, wherein the compound or the salt thereof is administered at a daily dosage of about 80 mg to about 100 mg, followed by a rest period of about 7 days, wherein the compound or the salt thereof is not administered.

33. The method of claim 9, wherein each cycle of the cyclical dosing schedule comprises a dosing period of about 21 days, wherein the compound or the salt thereof is administered at a daily dosage of about 120 mg, followed by a rest period of about 7 days, wherein the compound or the salt thereof is not administered.

34. The method of claim 9, wherein each cycle of the cyclical dosing schedule comprises a dosing period of about 21 days, wherein the compound or the salt thereof is administered at a daily dosage of about 160 mg, followed by a rest period of about 7 days, wherein the compound or the salt thereof is not administered.

35. The method of claim 9, wherein each cycle of the cyclical dosing schedule comprises a dosing period of about 21 days, wherein the compound or the salt thereof is administered at a daily dosage of about 210 mg, followed by a rest period of about 7 days, wherein the compound or the salt thereof is not administered.

36. The method of claim 9, wherein each cycle of the cyclical dosing schedule comprises a dosing period of about 21 days, wherein the compound or the salt thereof is administered at a daily dosage of about 90 mg, followed by a rest period of about 7 days, wherein the compound or the salt thereof is not administered.

37. The method of claim 9, wherein the liposarcoma has amplified MDM2 genes in its genome or overexpresses MDM2.

38. A method of treating a liposarcoma in a subject in need thereof, comprising orally administering to a subject at least one cycle of a cyclical dosing schedule of a compound of formula (I) or a pharmaceutically acceptable salt thereof

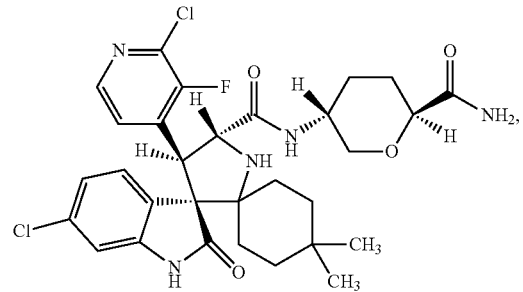

the cyclical dosing schedule comprising a dosing period of about 15 days to about 25 days, wherein the compound or the salt thereof is administered daily at a daily dosage of about 80 mg to about 250 mg, followed by a rest period of about 5 days to about 10 days, wherein the compound or the salt thereof is not administered.

* * * * *